(12) United States Patent
Lee et al.

(10) Patent No.: US 11,116,715 B2
(45) Date of Patent: *Sep. 14, 2021

(54) COMPOSITION FOR DERMAL INJECTION

(71) Applicants: CG Bio Co., Ltd., Seongnam-si (KR); DNCompany, Seoul (KR); Daewoong Pharmaceutical Co., Ltd., Seongnam-si (KR)

(72) Inventors: Ji Sun Lee, Seongnam-si (KR); Su Hyun Jung, Seongnam-si (KR); Hak Su Jang, Gwangju-si (KR); Jung Eun Choo, Seoul (KR); Hye Young Jung, Yongin-si (KR)

(73) Assignees: CG Bio Co., Ltd., Seongnam-si (KR); DNCompany, Seoul (KR); Daewoong Pharmaceutical Co., Ltd., Hwaseong-si (KR)

( * ) Notice: Subject to any disclaimer, the term of this patent is extended or adjusted under 35 U.S.C. 154(b) by 82 days.

This patent is subject to a terminal disclaimer.

(21) Appl. No.: 16/489,363

(22) PCT Filed: Feb. 27, 2018

(86) PCT No.: PCT/KR2018/002399
§ 371 (c)(1),
(2) Date: Aug. 28, 2019

(87) PCT Pub. No.: WO2018/159982
PCT Pub. Date: Sep. 7, 2018

(65) Prior Publication Data
US 2019/0374457 A1 Dec. 12, 2019

(30) Foreign Application Priority Data
Feb. 28, 2017 (KR) .......................... 10-2017-0026491

(51) Int. Cl.
*A61K 8/73* (2006.01)
*A61K 8/64* (2006.01)
*A61Q 19/08* (2006.01)

(52) U.S. Cl.
CPC .............. *A61K 8/735* (2013.01); *A61K 8/64* (2013.01); *A61Q 19/08* (2013.01); *A61K 2800/91* (2013.01)

(58) Field of Classification Search
CPC .................................. A61K 8/735; A61Q 19/08
See application file for complete search history.

(56) References Cited

U.S. PATENT DOCUMENTS 7,829,118 B1 11/2010 Gravett et al.
8,124,120 B2 * 2/2012 Sadozai ............... A61K 9/0024
424/426

9,017,712 B2 * 4/2015 Cho ..................... A61L 27/20
424/423
2013/0203856 A1 8/2013 Cho et al.
2014/0271507 A1 * 9/2014 Morris-Irvin ............ A61K 8/04
424/59

FOREIGN PATENT DOCUMENTS

| CN | 102552974 | 7/2012 |
| JP | 2020-508789 | 3/2020 |
| KR | 10-2011-0043730 | 4/2006 |
| KR | 10-2006-0127897 | 12/2006 |
| KR | 10-2012-0006451 | 1/2012 |
| KR | 10-2014-0000206 | 1/2014 |
| KR | 10-1660211 | 9/2016 |
| WO | WO 2018/159982 | 9/2018 |

OTHER PUBLICATIONS

International Search Report and the Written Opinion dated Jun. 4, 2018 From the International Searching Authority Re. Application No. PCT/KR2018/002399 and Its Translation of Search Report Into English. (17 pages).
Notice of Reasons for Rejection dated Jan. 18, 2021 From the Japan Patent Office Re. Application No. 2019-547686. (3 Pages).
Supplementary European Search Report and the European Search Opinion dated Nov. 24, 2020 From the European Patent Office Re. Application No. 18761692.5. (10 Pages).
Draelos "The Effect of a Combination of Recombinant EGF Cosmetic Serum and a Crosslinked Hyaluronic Acid Serum as Compared to a Fibroblast-Conditioned Media Serum on the Appearance of Aging Skin", Journal of Drugs in Dermatology, XP055750987, 15(6): 738-741, Jun. 1, 2016. Abstract.
Stocks et al. "Rheological Evaluation of the Physical Properties of Hyaluronic Acid Dermal Fillers", Journal of Drugs in Dermatology, XP055750519, 10(9): 974-980, Sep. 2011.
Tezel et al. "The Science of Hyaluronic Acid Dermal Fillers", Journal of Cosmetic and Laser Therapy, XP055248256, 10(1): 35-42, Mar. 2008.
Notification of Office Action and Search Report dated May 17, 2021 From the State Intellectual Property Office of the People's Republic of China Re. Application No. 201880014691.7. (8 Pages).

* cited by examiner

*Primary Examiner* — Bahar Craigo

(57) ABSTRACT

The present invention relates to a composition for dermal injection which includes two or more types of cross-linked hyaluronic acid particles having different particle diameters and non-cross-linked hyaluronic acid. The composition for dermal injection according to the present invention satisfies viscosity, extrusion force, and viscoelasticity conditions for dermal injection, and an extrusion force deviation is low so that the user does not feel fatigue when the composition is injected into the dermal thereof. Also, the composition is excellent in viscoelasticity and tissue restoring ability, is maintained for a long period of time, allows rapid recovery because an initial swelling degree is low, and also is excellent in safety and stability in the body.

12 Claims, No Drawings

COMPOSITION FOR DERMAL INJECTION

RELATED APPLICATIONS

This application is a National Phase of PCT Patent Application No. PCT/KR2018/002399 having International filing date of Feb. 27, 2018, which claims the benefit of priority of Korean Patent Application No. 10-2017-0026491 filed on Feb. 28, 2017. The contents of the above applications are all incorporated by reference as if fully set forth herein in their entirety.

FIELD AND BACKGROUND OF THE INVENTION

The present invention relates to a composition for dermal injection.

Hyaluronic acid, as a gel type product having transparency and viscosity, is a biodegradable and highly hydrophilic substance, and plays an important role in maintaining moisture in the dermal, dermal volume, and dermal elasticity because it attracts 214 water molecules per one molecule thereof. Thus, a filler containing a hyaluronic acid as an ingredient has been used for restoration of facial dermal elasticity, subtle improvement of a contour, reduction of facial wrinkles, and general cosmetic facial contouring procedures.

However, since natural hyaluronic acid has a half-life of only 1 to 2 days, the hyaluronic acid used in the filler is made in a cross-linking state to be maintained in the dermal for a long period of time. Here, the cross-linking results in preventing the degradation of hyaluronic acid caused by hyaluronidases and increasing viscosity to form volume (Song, Yi-Seop et al., Korean Journal of Dermatology 2014; 52(2):100~105).

Hyaluronic acid fillers currently available on the market are in the monophasic or biphasic form. A monophasic filler is composed of a homogeneous gel so that it has high viscosity, is smoothly injected, and is useful for forming a delicate shape. A biphasic filler is made in the form of a particle by filtering a gel using a sieve so that it has high elasticity, thus it is possible to maintain shape and increase volume.

Meanwhile, research on the development of a filler having ideal in vivo characteristics and surgical usefulness is continuing. However, a hyaluronic acid filler having excellent in vivo stability has high gel hardness and high viscosity so that it may be difficult to inject the filler through a fine gauge needle. Also, a hyaluronic acid filler capable of being easily injected through a fine gauge needle may have low in vivo stability. Accordingly, hyaluronic acid fillers excellent in both viscosity and elasticity are required.

SUMMARY OF THE INVENTION

The present invention is directed to providing a composition for dermal injection which includes two or more types of cross-linked hyaluronic acid particles having different particle diameters and non-cross-linked hyaluronic acid.

The present invention provides a composition for dermal injection which includes first cross-linked hyaluronic acid particles, second cross-linked hyaluronic acid particles having a different particle diameter from the first cross-linked hyaluronic acid particles, and non-cross-linked hyaluronic acid, wherein the first cross-linked hyaluronic acid particles and the second cross-linked hyaluronic acid particles are included in a weight ratio of 1:1.5 or more to 5.5 or less, and the first cross-linked hyaluronic acid particles and the non-cross-linked hyaluronic acid are included in a weight ratio of 1:0.1 or more to 1.2 or less.

DESCRIPTION OF SPECIFIC EMBODIMENTS OF THE INVENTION

The present invention relates to a composition for dermal injection which includes first cross-linked hyaluronic acid, second cross-linked hyaluronic acid having a different particle diameter from the first cross-linked hyaluronic acid, and non-cross-linked hyaluronic acid.

Hereinafter, the configurations of the present invention will be described in detail.

In the present invention, a composition for dermal injection may be denoted as a filler composition.

In the present invention, numerical values are presented using expressions such as "A or more", "A or less", "more than A" and "less than A", but in the case of numerical values given without such an expression, it is to be understood that the meaning of "A or more" or "A or less" is implied.

In the present invention, first cross-linked hyaluronic acid and second cross-linked hyaluronic acid may be denoted as first cross-linked hyaluronic acid particles and second cross-linked hyaluronic acid particles, respectively.

In the composition for dermal injection according to the present invention, the first cross-linked hyaluronic acid and the second cross-linked hyaluronic acid may be included in a weight ratio of 1:1.5 or more to 5.5 or less, and the first cross-linked hyaluronic acid particles and the non-cross-linked hyaluronic acid may be included in a weight ratio of 1:0.1 or more to 1.2 or less.

In an embodiment, the first cross-linked hyaluronic acid and the second cross-linked hyaluronic acid may be included in a weight ratio of 1:1.5 or more to less than 2.5, 1:2.5 or more to less than 3.5, 1:3.5 or more to less than 4.5, or 1:1.5 or more to less than 4.5.

In an embodiment, the first cross-linked hyaluronic acid particles and the non-cross-linked hyaluronic acid may be included in a weight ratio of 1:0.5 or more to 1.0 or less, 1:0.5 or more to 0.8 or less, or 1:0.5 or more to 0.7 or less.

Within the above ranges, properties required for the composition for dermal injection, such as viscosity, extrusion force, viscoelasticity, and the like, may be achieved.

Hyaluronic acid is a linear polymer including β-D-N-acetylglucosamine and β-D-glucuronic acid alternately bonded to each other, and may be interpreted as including all of hyaluronic acid itself, a salt thereof, and a combination thereof in the present invention. The hyaluronic acid may have a molecular weight of 100,000 to 5,000,000 Da or 1,000,000 to 1,500,000 Da, but the present invention is not limited thereto. Examples of the salt of hyaluronic acid include inorganic salts such as sodium hyaluronate, potassium hyaluronate, calcium hyaluronate, magnesium hyaluronate, zinc hyaluronate, cobalt hyaluronate, and the like and organic salts such as tetrabutylammonium hyaluronate and the like. In the present invention, as the hyaluronic acid, hyaluronic acid itself and a salt thereof may be used alone or in combination of two or more. The hyaluronic acid or the salt thereof may be isolated from a microorganism, synthesized, or commercially available, but the present invention is not limited thereto. For example, the hyaluronic acid may be isolated from *Streptococcus* sp. (*Streptococcus equi* or *Streptococcus zooepidemicus*) and purified.

In the present invention, the cross-linked hyaluronic acid particles may be used in the same sense as hydrated crosslinked hyaluronic acid particles. For example, it may mean that hyaluronic acid has been subjected to a crosslinking reaction through a covalent bond using a hydroxyl group. The moisture content or crosslinking ratio of hyaluronic acid may be adjusted through a common method used in the related art, and may be, for example, 10 to 20 mol % or 10 to 15 mol %.

The hyaluronic acid particles may be crosslinked by a crosslinking agent. The crosslinking agent may be, but is not limited to, ethylene glycol diglycidyl ether (EGDGE), 1,4-butanediol diglycidyl ether (BDDE), 1,6-hexanediol diglycidyl ether, propylene glycol diglycidyl ether, polypropylene glycol diglycidyl ether, diglycerol polyglycidyl ether, 1-ethyl-3-(3-dimethylaminopropyl)carbodiimide (EDC), divinyl sulfone (DVS), biscarbodiimide (BCDI), or a combination thereof.

The composition for dermal injection according to the present invention (hereinafter, also referred to as a hyaluronic acid composition) includes two or more types of cross-linked hyaluronic acid particles having different particle diameters.

In the present invention, the first cross-linked hyaluronic acid particle has lower elasticity and higher cohesion than those of the second cross-linked hyaluronic acid particle. For example, at a frequency of 0.01 Hz to 1 Hz, the first cross-linked hyaluronic acid particle may exhibit a G' value of less than 300 Pa and a tans value of 0.3 or more.

The $\tan\delta$ value is a G"/G' value (damping factor), which is a numerical value indicating whether the material is close to a solid or liquid state. Here, G' represents elastic modulus, and G" represents viscous modulus. A $\tan\delta$ value close to 1 at a frequency of 0.01 to 1 Hz may represent a solution state (low elasticity), and a $\tan\delta$ value close to 0 may represent an elastic body with high elasticity. Also, it has been reported that as a $\tan\delta$ value is low and the percentage of elasticity ($100\times G'/(G'+G")$) is high, the duration of a filler is expected to be long.

The first cross-linked hyaluronic acid particles may have an average particle diameter of 10 to 250 μm, specifically, 20 to 200 μm, 50 to 150 μm, 80 to 130 μm, 20 to 100 μm, 100 to 200 μm, 200 to 250 μm, 50 to 100 μm, or 150 to 200 μm.

In the present invention, the average particle diameter is D50 (50% diameter of particle), which means a particle size (volume) of a particle corresponding to the 50 percentile in the particle size distribution curve. Such an average particle diameter is measured using a particle size analyzer (Malvern, MS3000), and water is used as a dispersing solvent. That is, the average particle diameter represents a particle diameter of hydrated cross-linked hyaluronic acid particles.

In the present invention, properties of the second cross-linked hyaluronic acid particle are adjusted according to the size thereof. The second cross-linked hyaluronic acid particle has low viscosity and excellent elasticity compared to those of the first cross-linked hyaluronic acid. For example, at a frequency of 0.01 to 1 Hz, the second cross-linked hyaluronic acid particle may exhibit a G' value of 300 Pa or more and a tans value of less than 0.3.

The second cross-linked hyaluronic acid may have an average particle diameter of 300 to 700 μm, specifically 400 to 600 μm, 450 to 550 μm, 300 to 500 μm, 500 to 700 μm, or 400 to 700 μm.

The composition for dermal injection according to the present invention includes non-cross-linked hyaluronic acid. The non-cross-linked hyaluronic acid is in the form of a solution and may impart fluidity to the composition for dermal injection.

In the present invention, first cross-linked hyaluronic acid particles, second cross-linked hyaluronic acid particles, and non-cross-linked hyaluronic acid may be included at 1 to 10 parts by weight with respect to 100 parts by weight of the entire composition.

The composition for dermal injection according to the present invention may further include epidermal growth factor (EGF) in addition to the above-described components. The EGF may be injected into the dermal to stimulate the production of collagen, a fibroblast, and elastin, for example, to increase an effect of tissue restoration.

The EGF may be included at 0.0001 to 0.002 part by weight with respect to 100 parts by weight of the entire composition.

In addition, the composition for dermal injection according to the present invention may further include an anesthetic component. The anesthetic may alleviate pain experienced during injection of the composition.

Such an anesthetic component may be, but is not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, or a combination thereof.

The anesthetic component may be included at 0.1 to 1 part by weight with respect to 100 parts by weight of the composition.

The composition according to the present invention may be used with the addition of other common additives such as an antioxidant, a buffer solution and/or a bacteriostat, a diluent, a dispersant, a surfactant, a binder, a lubricant, or the like as necessary.

The composition for dermal injection according to the present invention may have the following physicochemical properties.

(a) no bubbles in appearance, colorlessness, and transparency;
(b) a pH of 7±1;
(c) a viscosity of 60,000 to 100,000 cP;
(d) an average osmotic pressure of 0.325 osmol/kg±10%;
(e) an extrusion force of 30 N or less;
(f) an elasticity of 70 to 95%; and
(g) a phase angle of 4 to 20°.

The viscosity is the amount that represents the magnitude of internal friction in a fluid, which is the resistance of the fluid to flow. Higher viscosity results in ease of injection and is useful for forming a delicate shape. For example, a monophasic hyaluronic acid filler has high viscosity so that it is smoothly injected and is useful for forming a delicate shape. In the present invention, viscosity may be measured using Brookfield DV3T according to conditions of experimental examples to be described below.

The composition for dermal injection according to the present invention may have a viscosity of 60,000 to 100,000 cP, 60,000 to 80,000 cP, or 60,000 to 72,000 cP.

The extrusion force means extrusion force at an injection rate at which a patient feels comfortable. The expression "a patient feels comfortable" is used to define an injection rate which does not cause injuries or excessive pain in a patient when the composition is injected into the dermal. The term "comfort" used herein encompasses the comfort or ability of a doctor or medical professional to inject the composition as well as the comfort of a patient. In the present invention, extrusion force may be measured using T0-101-161 commercially available from TestOne Co., Ltd. according to conditions of experimental examples to be described below. Generally, when extrusion force is low, there is no pressure pain during injection of the composition, and injection may be easily controlled.

The composition for dermal injection according to the present invention may have an extrusion force of 30 N or less or 25 N or less.

Viscoelasticity is the property of a material that exhibits both liquid and solid characteristics when a force is applied to the material. In the present invention, viscoelasticity may be measured using a rheometer according to conditions of experimental examples to be described below. Specifically, a force resisting an applied force and a loss of energy in the composition due to the applied force may be measured using a rheometer to determine viscous modulus, elastic modulus, and phase angle.

Elastic modulus (storage modulus; G') means the ratio of strain and stress which an elastic body has within the elastic limit. As the elastic modulus is higher, a composition is rigid and has a greater ability to resist strain.

The composition for dermal injection according to the present invention may have an elastic modulus of 500 to 1,500, 500 to 1,200, or 550 to 850.

Viscous modulus (loss modulus; G") is a measure of lost energy and pertains to a viscous component of a material.

The composition for dermal injection according to the present invention may have a viscous modulus of 100 to 200 or 150 to 190.

In addition, elasticity may be calculated using elastic modulus and viscous modulus values by the following formula. As the elasticity is higher, tissue restoring ability is excellent, and the duration of a filler is prolonged.

$$\text{Elasticity}(\%) = (100 \times G'/(G'+G''))$$

The composition for dermal injection according to the present invention may have an elasticity of 70 to 95% or 75 to 85%.

In addition, the phase angle is a measure of whether the composition is close to a liquid or solid state. As the phase angle is lower, the composition has solid characteristics, and as the phase angle is higher, the composition has liquid characteristics. In the case of a high phase angle, when deformation occurs due to a force applied from the outside or facial expression, the recovery to the original state is delayed, and the original shape is not maintained. In the case of a low phase angle, the G" value becomes smaller due to an instantaneous response to external deformation factors so that the composition is more like an elastic body than a fluid, and thus the composition does not flow out, and the original shape thereof may be continuously maintained. Thus, it is very important to appropriately maintain elasticity and phase angle values in the composition for dermal injection.

The composition for dermal injection according to the present invention may have a phase angle of 4 to 20° or 10 to 20°.

The composition for dermal injection according to the present invention may be prepared through a method commonly used in the related art.

In addition, the present invention provides a method of restoring tissue, which includes administering the above-described composition for dermal injection to a mammal.

The mammal may be a human.

The tissue restoration refers to temporarily or semi-permanently alleviating body wrinkles or restoring a wrinkle-free state, improving contours, forming volume in the tissue, or regenerating tissues such as in scar healing by injecting the composition. The dermal and tissue refer to those in the face, breast, hip, sexual organ, and other body regions.

In particular, the composition for dermal injection according to the present invention may be selected appropriately according to the degree of wrinkling of a user graded in accordance with the WSRS standard. The WSRS is an acronym for Wrinkle Severity Rating Scale, and classifies the degree of wrinkling of a human into 5 grades (Grades 1 to 5). The Grades 1 to 5 are absence (no of folds), mild (shallow folds), moderate (moderate folds), severe (deep folds), and extreme (very deep folds), respectively. Detailed contents of the WSRS and each grade are described in a document by Am J Clin Dermatol 2004; 5 (1): 49-52 1175-0561, and the present invention can evaluate wrinkles in accordance with the WSRS using a method presented in the document.

Meanwhile, the Ministry of Food and Drug Safety in Korea also classifies the wrinkling degree into mild, moderate, severe, and extreme according to the WSRS through guidelines for approval and review of a dermal cosmetic filler based on a hyaluronic acid raw material issued on December 2017, which proposes to include information on wrinkling degree in describing the purpose of a dermal cosmetic filler.

The composition according to the present invention may be used for mild folds of Grade 2 or moderate folds of Grade 3 in the WSRS.

In addition, a syringe may be filled with the composition for dermal injection to inject the composition into the layers of dermal.

The layers of dermal are classified into the epidermis, dermis, and hypodermis. The composition for dermal injection according to the present invention may be injected into superficial dermis or mid-dermis.

Hereinafter, the present invention will be described in more detail with reference to embodiment examples of the present invention. However, the following examples are merely presented to exemplify the present invention, and the content of the present invention is not limited to the following examples. That is, the examples of the present invention serve to complete the disclosure of the present invention, and are provided to make known the full scope of the invention to those of ordinary knowledge and skill in the art to which this invention pertains. This invention should be defined based on the scope of the appended claims.

EXAMPLES

Reference Example. Measurement of Properties (1) Viscosity Measurement

The viscosity was measured according to a viscosity measurement method among the general test methods of the Korean Pharmacopoeia.

Specifically, 500 ul of a composition sample was loaded in a sample cup of a viscometer (DV3T, Brookfield), the sample cup was installed in a CP-52 sample cup, and the rotational speed of the spindle was then set to 2 rpm to measure viscosity.

(2) Extrusion Force Measurement

A compression test was performed using a universal testing machine (T0-101-161, TestOne).

Specifically, a syringe was filled with a composition sample, a 27G ½-inch needle was installed in the syringe, and the syringe was then set in a jig. Afterward, a speed of 50 mm/min and a displacement of 25 mm were set to perform a compression test.

(3) Viscoelasticity Measurement

Rheological properties were measured using a rheometer.

Specifically, a sample was placed between parallel plates, a force resistant to an applied force and a loss of energy were measured while vibrating and rotating the parallel plates to determine the elastic modulus (G'), viscous modulus (G"), and phase angle of the sample.

Conditions for rheometer analysis are as follows.
Frequency: 1 Hz
Temperature: 25° C.
Strain: 5%
Measuring geometry: 20 mm plate
Measuring gap: 0.5 mm
Measuring mode: oscillation mode In addition, elasticity was calculated by the following formula with reference to the measured G' and G" values.

$$\text{Elasticity}(\%) = (100 \times G'/(G'+G''))$$

Preparation Examples 1-1 to 1-20

(1) Preparation of First Cross-Linked Hyaluronic Acid Particles 10 g of sodium hyaluronate, 81 g of purified water, and 9 g of 1 M sodium hydroxide (1M NaOH) were stirred at 400 rpm under vacuum until the mixture became a transparent gel without granules. Then, 0.5 g of butanediol diglycidyl ether (BDDE) as a crosslinking agent was added thereto and stirred. After the stirring was completed, the container was sealed and a crosslinking reaction was performed under conditions of 80 rpm and 50° C. for 1 hour. Then, a resulting substance was allowed to stand at 27° C. for 16 hours to prepare a gel.

Afterward, the gel thus obtained was input into 30 L of a 0.9× phosphate buffered saline (PBS) solution, and then the PBS solution was exchanged with a new one every 3 hours (3 times/day for 5 days) to eliminate a residual reagent. Then, a resulting substance was passed through a mortar grinder (RS 200 commercially available from Retsch GmbH) for 40 minutes to prepare first cross-linked hyaluronic acid particles.

The first cross-linked hyaluronic acid particles thus prepared had an average particle diameter of about 200 μm.

(2) Preparation of Second Cross-Linked Hyaluronic Acid Particles 20 g of sodium hyaluronate, 117 g of purified water, and 13 g of 1M NaOH were stirred at 400 rpm under vacuum until the mixture became a transparent gel without granules. Then, 1 g of BDDE as a crosslinking agent was added thereto and stirred. After the stirring was completed, the container was sealed and a crosslinking reaction was performed under conditions of 80 rpm and 50° C. for 1 hour. Then, a resulting substance was allowed to stand at 27° C. for 16 hours to prepare a gel.

Afterward, the gel thus obtained was input into 30 L of a 0.9× PBS solution, and then the PBS solution was exchanged with a new one every 3 hours (3 times/day for 5 days) to eliminate a residual reagent. Then, a resulting substance was passed through a 200 μm standard test sieve to prepare second cross-linked hyaluronic acid particles.

The second cross-linked hyaluronic acid particles thus prepared had an average particle diameter of about 300 to 700 μm.

(3) Preparation of Non-Cross-Linked Hyaluronic Acid 2 g of sodium hyaluronate was added to 100 g of purified water and stirred to prepare 2% non-cross-linked hyaluronic acid.

(4) Preparation of Hyaluronic Acid Composition

The first cross-linked hyaluronic acid particles prepared in step (1), the second cross-linked hyaluronic acid particles prepared in step (2), and the non-cross-linked hyaluronic acid were mixed in contents (g) and content ratios as shown in the following Table 1 to prepare hyaluronic acid compositions.

TABLE 1

| | First cross-linked hyaluronic acid particle | | Second cross-linked hyaluronic acid particle | | Non-cross-linked hyaluronic acid | |
|---|---|---|---|---|---|---|
| | Content | Content ratio | Content | Content ratio | Content | Content ratio |
| Preparation Example 1-1 | 10 | 1 | 20 | 2 | 2 | 0.2 |
| Preparation Example 1-2 | 10 | 1 | 20 | 2 | 4 | 0.4 |
| Preparation Example 1-3 | 10 | 1 | 20 | 2 | 6 | 0.6 |
| Preparation Example 1-4 | 10 | 1 | 20 | 2 | 8 | 0.8 |
| Preparation Example 1-5 | 10 | 1 | 20 | 2 | 10 | 1.0 |
| Preparation Example 1-6 | 10 | 1 | 30 | 3 | 2 | 0.2 |
| Preparation Example 1-7 | 10 | 1 | 30 | 3 | 4 | 0.4 |
| Preparation Example 1-8 | 10 | 1 | 30 | 3 | 6 | 0.6 |
| Preparation Example 1-9 | 10 | 1 | 30 | 3 | 8 | 0.8 |
| Preparation Example 1-10 | 10 | 1 | 30 | 3 | 10 | 1.0 |
| Preparation Example 1-11 | 10 | 1 | 40 | 4 | 2 | 0.2 |
| Preparation Example 1-12 | 10 | 1 | 40 | 4 | 4 | 0.4 |
| Preparation Example 1-13 | 10 | 1 | 40 | 4 | 6 | 0.6 |
| Preparation Example 1-14 | 10 | 1 | 40 | 4 | 8 | 0.8 |
| Preparation Example 1-15 | 10 | 1 | 40 | 4 | 10 | 1.0 |
| Preparation Example 1-16 | 10 | 1 | 50 | 5 | 2 | 0.2 |
| Preparation Example 1-17 | 10 | 1 | 50 | 5 | 4 | 0.4 |
| Preparation Example 1-18 | 10 | 1 | 50 | 5 | 6 | 0.6 |
| Preparation Example 1-19 | 10 | 1 | 50 | 5 | 8 | 0.8 |
| Preparation Example 1-20 | 10 | 1 | 50 | 5 | 10 | 1.0 |

Comparative Preparation Examples 2-1 to 2-10

As comparative examples of the compositions including all of first cross-linked hyaluronic acid particles, second cross-linked hyaluronic acid particles, and non-cross-linked hyaluronic acid, hyaluronic acid compositions were prepared in the same manner as Preparation Example 1 except that the first cross-linked hyaluronic acid particles, second cross-linked hyaluronic acid particles, and non-cross-linked hyaluronic acid were mixed in contents (g) and content ratios as shown in the following Table 2.

TABLE 2

|  | First cross-linked hyaluronic acid particle | | Second cross-linked hyaluronic acid particle | | Non-cross-linked hyaluronic acid | |
|---|---|---|---|---|---|---|
|  | Content | Content ratio | Content | Content ratio | Content | Content ratio |
| Comparative Preparation Example 2-1 | 10 | 1 | 0 | 0 | 0 | 0 |
| Comparative Preparation Example 2-2 | 10 | 1 | 10 | 1 | 0 | 0 |
| Comparative Preparation Example 2-3 | 10 | 1 | 20 | 2 | 0 | 0 |
| Comparative Preparation Example 2-4 | 10 | 1 | 30 | 3 | 0 | 0 |
| Comparative Preparation Example 2-5 | 10 | 1 | 40 | 4 | 0 | 0 |
| Comparative Preparation Example 2-6 | 10 | 1 | 50 | 5 | 0 | 0 |
| Comparative Preparation Example 2-7 | 0 | 0 | 10 | 1 | 0 | 0 |
| Comparative Preparation Example 2-8 | 0 | 0 | 10 | 1 | 2 | 0.2 |
| Comparative Preparation Example 2-9 | 0 | 0 | 10 | 1 | 4 | 0.4 |
| Comparative Preparation Example 2-10 | 0 | 0 | 10 | 1 | 6 | 0.6 |

Comparative Preparation Examples 3-1 to 3-5

Hyaluronic acid compositions were prepared in the same manner as Preparation Example 1 except that the first cross-linked hyaluronic acid particles, second cross-linked hyaluronic acid particles, and non-cross-linked hyaluronic acid were mixed in contents (g) and content ratios as shown in the following Table 3.

TABLE 3

|  | First cross-linked hyaluronic acid particle | | Second cross-linked hyaluronic acid particle | | Non-cross-linked hyaluronic acid | |
|---|---|---|---|---|---|---|
|  | Content | Content ratio | Content | Content ratio | Content | Content ratio |
| Comparative Preparation Example 3-1 | 10 | 1 | 10 | 1 | 2 | 0.2 |
| Comparative Preparation Example 3-2 | 10 | 1 | 10 | 1 | 4 | 0.4 |
| Comparative Preparation Example 3-3 | 10 | 1 | 10 | 1 | 6 | 0.6 |
| Comparative Preparation Example 3-4 | 10 | 1 | 10 | 1 | 8 | 0.8 |
| Comparative Preparation Example 3-5 | 10 | 1 | 10 | 1 | 10 | 1.0 |

Experimental Example 1

Viscosity and Extrusion Force Measurement

Measurement results of viscosity and extrusion force are shown in the following Tables 4 to 6.

The measurement of viscosity and extrusion force was performed three times using each sample, and average values of three measurements were shown.

TABLE 4

|  | First cross-linked hyaluronic acid particle | Second cross-linked hyaluronic acid particle | Non-cross-linked hyaluronic acid | Viscosity (cP) | Extrusion force (N) |
|---|---|---|---|---|---|
| Preparation Example 1-1 | 1 | 2 | 0.2 | 78814 | 21.33 |
| Preparation Example 1-2 | 1 | 2 | 0.4 | 72166 | 19.25 |
| Preparation Example 1-3 | 1 | 2 | 0.6 | 70397 | 13.58 |
| Preparation Example 1-4 | 1 | 2 | 0.8 | 66202 | 11.78 |
| Preparation Example 1-5 | 1 | 2 | 1.0 | 61825 | 10.69 |
| Preparation Example 1-6 | 1 | 3 | 0.2 | 82970 | 22.03 |
| Preparation Example 1-7 | 1 | 3 | 0.4 | 82540 | 17.84 |
| Preparation Example 1-8 | 1 | 3 | 0.6 | 77700 | 15.08 |

TABLE 4-continued

|  | First cross-linked hyaluronic acid particle | Second cross-linked hyaluronic acid particle | Non-cross-linked hyaluronic acid | Viscosity (cP) | Extrusion force (N) |
| --- | --- | --- | --- | --- | --- |
| Preparation Example 1-9 | 1 | 3 | 0.8 | 71857 | 14.73 |
| Preparation Example 1-10 | 1 | 3 | 1.0 | 71990 | 14.02 |
| Preparation Example 1-11 | 1 | 4 | 0.2 | 85880 | 25.70 |
| Preparation Example 1-12 | 1 | 4 | 0.4 | 78472 | 20.60 |
| Preparation Example 1-13 | 1 | 4 | 0.6 | 77579 | 15.51 |
| Preparation Example 1-14 | 1 | 4 | 0.8 | 75407 | 15.27 |
| Preparation Example 1-15 | 1 | 4 | 1.0 | 76840 | 11.61 |
| Preparation Example 1-16 | 1 | 5 | 0.2 | 94237 | 29.29 |
| Preparation Example 1-17 | 1 | 5 | 0.4 | 80335 | 19.43 |
| Preparation Example 1-18 | 1 | 5 | 0.6 | 80765 | 15.65 |
| Preparation Example 1-19 | 1 | 5 | 0.8 | 91084 | 13.04 |
| Preparation Example 1-20 | 1 | 5 | 1.0 | 84701 | 15.58 |

TABLE 5

|  | First cross-linked hyaluronic acid particle | Second cross-linked hyaluronic acid particle | Non-cross-linked hyaluronic acid | Viscosity (cP) | Extrusion force (N) |
| --- | --- | --- | --- | --- | --- |
| Comparative Preparation Example 2-1 | 1 | 0 | 0 | 25896 | 31.12 |
| Comparative Preparation Example 2-2 | 1 | 1 | 0 | 80170 | 74.35 |
| Comparative Preparation Example 2-3 | 1 | 2 | 0 | 105460 | 112.66 |
| Comparative Preparation Example 2-4 | 1 | 3 | 0 | 118182 | 121.24 |
| Comparative Preparation Example 2-5 | 1 | 4 | 0 | 140016 | 132.97 |
| Comparative Preparation Example 2-6 | 1 | 5 | 0 | 147077 | 125.77 |
| Comparative Preparation Example 2-7 | 0 | 1 | 0 | 26624 | 19.49 |
| Comparative Preparation Example 2-8 | 0 | 1 | 0.2 | 18587 | 10.32 |
| Comparative Preparation Example 2-9 | 0 | 1 | 0.4 | 17804 | 9.25 |
| Comparative Preparation Example 2-10 | 0 | 1 | 0.6 | 24717 | 6.68 |

TABLE 6

|  | First cross-linked hyaluronic acid particle | Second cross-linked hyaluronic acid particle | Non-cross-linked hyaluronic acid | Viscosity (cP) | Extrusion force (N) |
|---|---|---|---|---|---|
| Comparative Preparation Example 3-1 | 1 | 1 | 0.2 | 57096 | 16.94 |
| Comparative Preparation Example 3-2 | 1 | 1 | 0.4 | 50249 | 13.78 |
| Comparative Preparation Example 3-3 | 1 | 1 | 0.6 | 43844 | 16.84 |
| Comparative Preparation Example 3-4 | 1 | 1 | 0.8 | 42146 | 12.35 |
| Comparative Preparation Example 3-5 | 1 | 1 | 1.0 | 38630 | 11.58 |

As shown in Table 5, when only first cross-linked hyaluronic acid particles were used (Comparative Preparation Example 2-1) or when second cross-linked hyaluronic acid particles and non-cross-linked hyaluronic acid were used without first cross-linked hyaluronic acid, viscosity was low, thus it is difficult to apply these compositions to a filler.

In addition, when first and second cross-linked hyaluronic acid particles were used without non-cross-linked hyaluronic acid, extrusion force increased, thus there is a possibility of a problem in use occurring.

However, as shown in Table 4, when all of first cross-linked hyaluronic acid particles, second cross-linked hyaluronic acid particles, and non-cross-linked hyaluronic acid were included, filler compositions which satisfy both viscosity and extrusion force can be obtained.

In particular, when first cross-linked hyaluronic acid particles and second cross-linked hyaluronic acid particles were included in a weight ratio of 1:1.5 or more to less than 2.5, and first cross-linked hyaluronic acid particles and non-cross-linked hyaluronic acid particles were included at a weight ratio of 1:0.5 or more to 1.0 or less (Preparation Examples 1-3 to 1-5), a viscosity of 60,000 to 80,000 cP, specifically 60,000 to 72,000 cP, and an extrusion force of 25 N or less were exhibited, thus these compositions are suitable for the purpose of tissue restoration.

In addition, as shown in Table 6, when a content ratio of second cross-linked hyaluronic acid particles was 1.5 or less, a low viscosity of less than 60,000 cP was exhibited, thus it is difficult to apply these compositions to a filler.

Experimental Example 2

Viscoelasticity Measurement

Measurement results of elasticity, elastic modulus (G'), viscous modulus (G"), and phase angle were shown in the following Tables 7 to 9.

The measurement of viscoelasticity was performed three times using each sample, and an average value of three measurements was shown.

TABLE 7

|  | First cross-linked hyaluronic acid particle | Second cross-linked hyaluronic acid particle | Non-cross-linked hyaluronic acid | Elasticity | G' | G" | Phase angle |
|---|---|---|---|---|---|---|---|
| Preparation Example 1-1 | 1 | 2 | 0.2 | 89.88 | 1177 | 132.5 | 6.43 |
| Preparation Example 1-2 | 1 | 2 | 0.4 | 86.63 | 1032 | 159.3 | 8.77 |
| Preparation Example 1-3 | 1 | 2 | 0.6 | 83.19 | 823 | 166.3 | 11.42 |
| Preparation Example 1-4 | 1 | 2 | 0.8 | 78.06 | 633.2 | 178 | 15.70 |
| Preparation Example 1-5 | 1 | 2 | 1.0 | 75.27 | 554.8 | 182.3 | 18.20 |
| Preparation Example 1-6 | 1 | 3 | 0.2 | 88.53 | 1209 | 156.7 | 7.39 |
| Preparation Example 1-7 | 1 | 3 | 0.4 | 86.87 | 1098 | 165.9 | 8.59 |
| Preparation Example 1-8 | 1 | 3 | 0.6 | 84.32 | 904.3 | 168.1 | 10.53 |
| Preparation Example 1-9 | 1 | 3 | 0.8 | 82.13 | 817.7 | 177.9 | 12.27 |
| Preparation Example 1-10 | 1 | 3 | 1.0 | 81.33 | 801 | 183.9 | 12.93 |
| Preparation Example 1-11 | 1 | 4 | 0.2 | 89.10 | 1255 | 153.5 | 6.98 |

TABLE 7-continued

| | First cross-linked hyaluronic acid particle | Second cross-linked hyaluronic acid particle | Non-cross-linked hyaluronic acid | Elasticity | G' | G" | Phase angle |
|---|---|---|---|---|---|---|---|
| Preparation Example 1-12 | 1 | 4 | 0.4 | 86.65 | 1170 | 180.3 | 8.76 |
| Preparation Example 1-13 | 1 | 4 | 0.6 | 84.96 | 1065 | 188.5 | 10.04 |
| Preparation Example 1-14 | 1 | 4 | 0.8 | 84.28 | 953.8 | 177.9 | 10.56 |
| Preparation Example 1-15 | 1 | 4 | 1.0 | 83.26 | 924.9 | 186 | 11.37 |
| Preparation Example 1-16 | 1 | 5 | 0.2 | 92.60 | 1383 | 110.6 | 4.57 |
| Preparation Example 1-17 | 1 | 5 | 0.4 | 91.66 | 1332 | 121.2 | 5.20 |
| Preparation Example 1-18 | 1 | 5 | 0.6 | 90.62 | 1333 | 137.9 | 5.91 |
| Preparation Example 1-19 | 1 | 5 | 0.8 | 86.62 | 1095 | 169.2 | 8.78 |
| Preparation Example 1-20 | 1 | 5 | 1.0 | 85.68 | 1137 | 190 | 9.49 |

TABLE 8

| | First cross-linked hyaluronic acid particle | Second cross-linked hyaluronic acid particle | Non-cross-linked hyaluronic acid | Elasticity | G' | G" | Phase angle |
|---|---|---|---|---|---|---|---|
| Comparative Preparation Example 2-1 | 1 | 0 | 0 | 87.80 | 140.70 | 19.55 | 7.91 |
| Comparative Preparation Example 2-2 | 1 | 1 | 0 | 89.21 | 854.40 | 103.30 | 6.89 |
| Comparative Preparation Example 2-3 | 1 | 2 | 0 | 91.02 | 1158.00 | 114.30 | 5.64 |
| Comparative Preparation Example 2-4 | 1 | 3 | 0 | 91.44 | 1314.00 | 123.00 | 5.35 |
| Comparative Preparation Example 2-5 | 1 | 4 | 0 | 93.60 | 1359 | 92.96 | 3.91 |
| Comparative Preparation Example 2-6 | 1 | 5 | 0 | 93.90 | 1413 | 91.79 | 3.72 |
| Comparative Preparation Example 2-7 | 0 | 1 | 0 | 93.09 | 1839.00 | 136.50 | 4.24 |
| Comparative Preparation Example 2-8 | 0 | 1 | 0.2 | 84.17 | 846.20 | 159.10 | 10.65 |
| Comparative Preparation Example 2-9 | 0 | 1 | 0.4 | 71.79 | 319.90 | 125.70 | 21.45 |
| Comparative Preparation Example 2-10 | 0 | 1 | 0.6 | 67.56 | 72.11 | 34.62 | 25.65 |

TABLE 9

| | First cross-linked hyaluronic acid particle | Second cross-linked hyaluronic acid particle | Non-cross-linked hyaluronic acid | Elasticity | G' | G" | Phase angle |
|---|---|---|---|---|---|---|---|
| Comparative Preparation Example 3-1 | 1 | 1 | 0.2 | 84.16 | 660.5 | 124.3 | 10.66 |
| Comparative Preparation Example 3-2 | 1 | 1 | 0.4 | 78.28 | 568.5 | 157.7 | 15.51 |
| Comparative Preparation Example 3-3 | 1 | 1 | 0.6 | 75.58 | 484 | 156.4 | 17.91 |
| Comparative Preparation Example 3-4 | 1 | 1 | 0.8 | 68.57 | 278.8 | 127.8 | 24.64 |
| Comparative Preparation Example 3-5 | 1 | 1 | 1.0 | 66.07 | 251 | 128.9 | 27.18 |

As shown in Table 7, when all of first cross-linked hyaluronic acid particles, second cross-linked hyaluronic acid particles, and non-cross-linked hyaluronic acid were included, hyaluronic acid compositions which satisfy both elasticity and phase angle can be obtained.

Also, when cross-linked hyaluronic acid was included without non-cross-linked hyaluronic acid, the phase angle value was low so that the composition had high solid characteristics, thus these compositions are not suitable for use as filler.

Meanwhile, when first cross-linked hyaluronic acid particles and second cross-linked hyaluronic acid particles were included in a weight ratio of 1:1 to 2 (Comparative Preparation Examples 3-1 to 3-5), elasticity and phase angle values were similar to those of the preparation examples, but G' values were low, thus the use of these compositions as filler compositions is limited.

A composition for dermal injection according to the present invention satisfies viscosity, extrusion force, and viscoelasticity conditions for dermal injection, and an extrusion force deviation is low so that the user does not feel fatigue when the composition is injected into the dermal thereof.

Also, the composition is excellent in viscoelasticity and tissue restoring ability, is maintained for a long period of time, allows rapid recovery because an initial swelling degree is low, and also is excellent in safety and stability in the body.

What is claimed is:

1. A composition for dermal injection, comprising first cross-linked hyaluronic acid particles, second cross-linked hyaluronic acid particles having different particle diameters from the first cross-linked hyaluronic acid particles, and non-cross-linked hyaluronic acid,
   wherein the first cross-linked hyaluronic acid particles and the second cross-linked hyaluronic acid particles are included in a weight ratio of 1: 1.5 or more to 5.5 or less, and
   the first cross-linked hyaluronic acid particles and the non-cross-linked hyaluronic acid are included in a weight ratio of 1: 0.1 or more to 1.2 or less,
   the first cross-linked hyaluronic acid particles have an average particle diameter of 10 to 250 μm, and
   the second cross-linked hyaluronic acid particles have an average particle diameter of 300 to 700 μm.

2. The composition of claim 1, wherein the first cross-linked hyaluronic acid particle, the second cross-linked hyaluronic acid particle, or the non-cross-linked hyaluronic acid has a molecular weight of 1,000,000 to 1,500,000 Da.

3. The composition of claim 1, wherein the first cross-linked hyaluronic acid particle or the second cross-linked hyaluronic acid particle has a degree of crosslinking of 10 to 20 mol %.

4. The composition of claim 1, wherein the first cross-linked hyaluronic acid particles, the second cross-linked hyaluronic acid particles, and the non-cross-linked hyaluronic acid are included at 1 to 10 parts by weight with respect to 100 parts by weight of the entire composition.

5. The composition of claim 1, further comprising epidermal growth factor (EGF).

6. The composition of claim 5, wherein the epidermal growth factor (EGF) is included at 0.0001 to 0.002 part by weight with respect to 100 parts by weight of the entire composition.

7. The composition of claim 1, further comprising an anesthetic component.

8. The composition of claim 7, wherein the anesthetic component is included at 0.1 to 1 part by weight with respect to 100 parts by weight of the composition.

9. The composition of claim 1, wherein the composition for dermal injection has the following physicochemical properties:
   (a) no bubbles in appearance, colorlessness, and transparency,
   (b) a pH of 7±1,
   (c) a viscosity of 60,000 to 100,000 cP,
   (d) an average osmotic pressure of 0.325 osmol/kg±10%,
   (e) an extrusion force of 30 N or less,
   (f) an elasticity of 70 to 95%, and
   (g) a phase angle of 4 to 20°.

10. The composition of claim 9, wherein the composition for dermal injection has a viscosity of 60,000 to 72,000 cP.

11. The composition of claim 9, wherein the composition for dermal injection has an extrusion force of 25 N or less.

12. The composition of claim 9, wherein the composition for dermal injection has an elasticity of 75 to 85% and a phase angle of 10 to 20°.

* * * * *